US00PP30207P2

(12) United States Plant Patent
Meilland

(10) Patent No.: US PP30,207 P2
(45) Date of Patent: Feb. 19, 2019

(54) HYBRID TEA ROSE PLANT NAMED 'MEIZOLNIL'

(50) Latin Name: *Rosa hybrida*
Varietal Denomination: MEIZOLNIL

(71) Applicant: THE CONARD-PYLE COMPANY, West Grove, PA (US)

(72) Inventor: Alain Antoine Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/732,094

(22) Filed: Sep. 18, 2017

(51) Int. Cl.
*A01H 5/02* (2018.01)

(52) U.S. Cl.
USPC ..... Plt./138
CPC ..... *A01H 5/02* (2013.01)

(58) Field of Classification Search
USPC ..... Plt./138
CPC ..... A01H 5/0222
See application file for complete search history.

(56) References Cited

U.S. PATENT DOCUMENTS

PP5,067 P 7/1983 Meilland
PP6,262 P 8/1988 Stephens et al.

*Primary Examiner* — Kent L Bell
(74) *Attorney, Agent, or Firm* — Buchanan Ingersoll & Rooney PC

(57) ABSTRACT

A new and distinct variety of Hybrid Tea Rose plant, herein referred to by its cultivar name, 'MEIZOLNIL', is provided which forms in abundance on a nearly continuous basis attractive, cup-shaped, dark pink colored blossoms which emit a very pleasant strong fragrance. Attractive, glossy, rather dense foliage is formed. The disease tolerance is good, particularly against Oidium and mildew. The new variety is well suited for proving attractive ornamentation in the landscape.

1 Drawing Sheet

Figures 1, 2, 3, 4, 5, 6, 7, 8, 9, 10, 11, 12, 13, 14, 15:
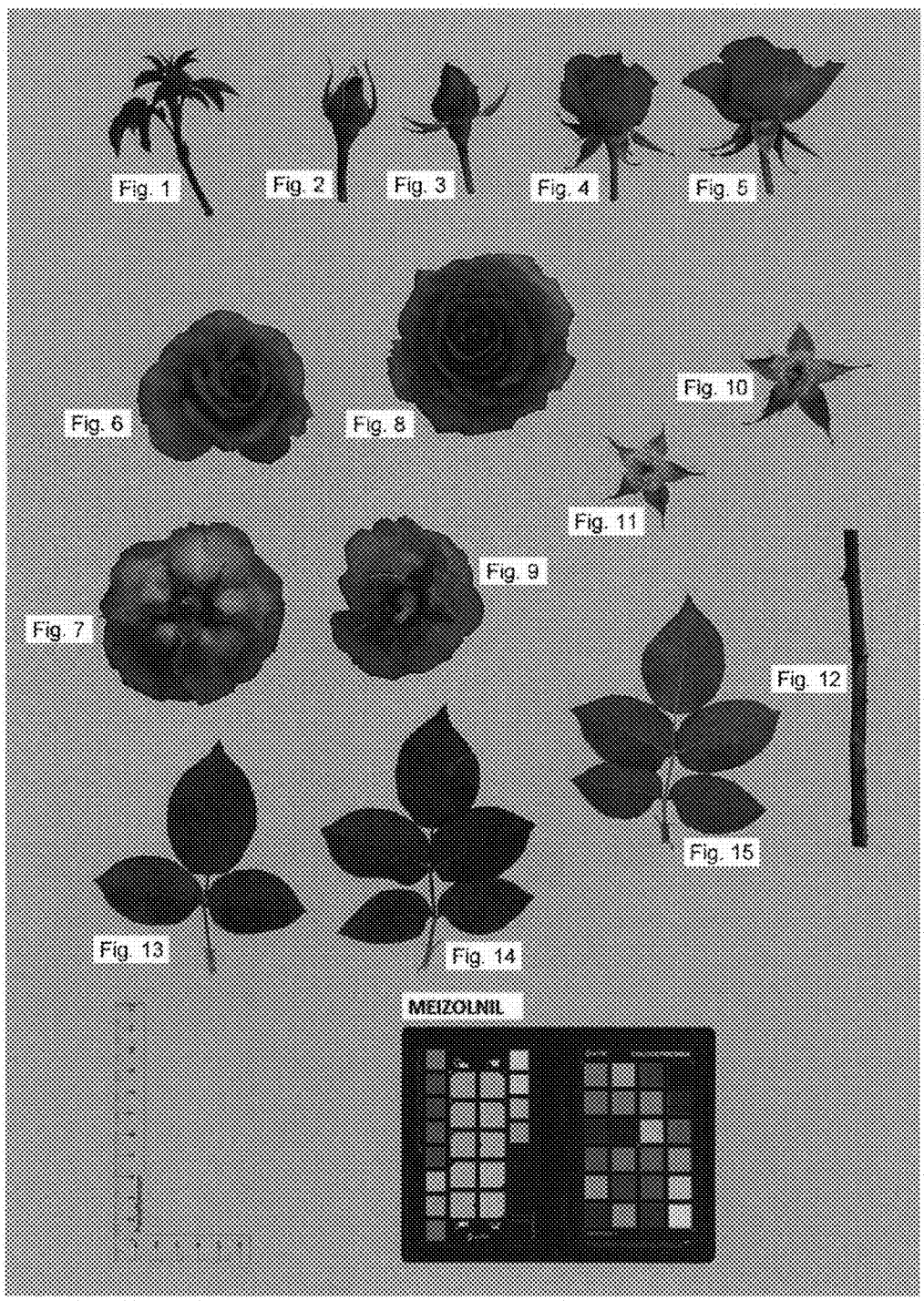

Botanical/commercial classification:
Latin name—*Rosa hybrida.*
Common name—Hybrid Tea Rose Plant.
Varietal denomination: 'MEIZOLNIL'.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the product of the cross of the 'STEBIGPU' variety (U.S. Plant Pat. No. 6,262) and 'MEIMAGARMIC' variety (U.S. Plant Pat. No. 5,067). The male parent (i.e, the pollen parent) was the 'ADHARMAN' variety (non-patented in the United States).

The parentage of the new variety can be summarized as follows:

('STEBIGPU' x 'MEIMAGARMIC') x 'ADHARMAN'

The seeds resulting from the above pollination were sown and small plants were obtained which were physically and biologically different from each other. Selective study resulted in the identification of a single plant of the new variety.

It was found that the new variety of Hybrid Tea rose plant of the present invention:

(a) very abundantly and nearly continuously forms attractive, cup-shaped, dark pink blossoms which emit a very pleasant strong fragrance,
(b) forms attractive, rather dense, glossy foliage, (c) exhibits good tolerance to diseases, particularly against Oidium and mildew, and
(d) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'STEBIGPU' variety is less resistant to Oidium. The 'MEIMAGARMIC' variety displays white colored blossoms bordered with pink, and the 'ADHARMAN' variety (i.e, the pollen parent) displays red colored blossoms, while the new variety displays dark pink colored blossoms. Additionally, the ('STEBIGPU' x 'MEIMAGARMIC') variety (i.e., the seed parent) displays light pink colored flowers unlike the dark pink colored flowers of the new variety.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'MEIZOLNIL'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during June while budded on *Rosa laxa* and growing outdoors at Le Gannet des Maures, Var, France. Standard color information and dimensions in centimeters are included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening of the petals.

FIG. 5—illustrates a specimen of a flower in the course of opening.

FIG. 6—illustrates a specimen of a flower in the course of opening—plan view—obverse.

FIG. 7—illustrates a specimen of a flower in the course of opening—plan view—reverse.

FIG. 8—illustrates a specimen of a fully open flower—plan view—obverse.

FIG. 9—illustrates a specimen of a fully open flower—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 3 leaflets—plan view—upper surface.

FIG. 14—illustrates a specimen of a leaf with 5 leaflets—plan view—upper surface.

FIG. 15—illustrates a specimen of a leaf with 5 leaflets—plan view—under surface.

DETAILED BOTANICAL DESCRIPTION

The chart used in the identification of the colors is that of The Royal Horticultural Society (R.H.S. Color Chart), 2001, London, England. The terminology which precedes reference to the chart has been added to indicate the corresponding color in more common terms. The description is based on the observation of two-year-old specimens of the new variety during June while budded on their *Rosa laxa* and growing outdoors at Le Gannet des Maures, Var, France.

Class: Hybrid Tea Rose Plant.

Plant:

*Habit*.—Semi-erect.

*Height*.—Approximately 70 to 90 cm on average.

*Diameter*.—Approximately 50 cm on average.

Branches:

*Color*.—Young stems: commonly near Yellow-Green Group 144B. Adult wood: commonly near Yellow-Green Group 144A.

*Thorns*.—Configuration on adult stems: curved downward on the upper surface and concave on the under surface. Long prickles (≥0.6 cm) — quantity: commonly approximately 13 thorns per 10 cm long young stem and commonly 9 thorns per 10 cm long adult stem. Long prickles (≥0.6 cm) — base shape: oval. Long prickles (≥0.6 cm) — size: commonly approximately 0.6 to 0.8 cm in length on average on young stems and commonly approximately 0.6 to 0.9 cm in length on average on adult stems. Long prickles (≥0.6 cm) — color commonly near Yellow-Green Group 152D on young stems and commonly near Greyed-Orange Group 166A to 166B on adult stems. Small prickles (<0.6 cm) — quantity: commonly approximately 72 thorns per 10 cm long young stem and commonly 11 thorns per 10 cm long adult stem. Small prickles (<0.6 cm) — base shape: oval. Small prickles (<0.6 cm) — size: commonly approximately 0.1 to 0.4 cm in length on average. Small prickles (<0.6 cm) — color: commonly near Yellow-Green Group 152D on young stems and commonly near Greyed-Orange Group 175B on adult stems.

Foliage:

*General appearance*.—Rather dense with a glossy aspect.

*Leaf*.—Length: approximately 11 to 13 cm on average. Width: approximately 8 to 10 cm on average.

*Number of leaflets*.—3, 5, and 7; most often 5 or 7.

*Terminal leaflet*.—Length: approximately 5.5 to 6.5 cm on average. Width: approximately 3.0 to 3.5 cm on average.

*New foliage*.—Upper surface color: commonly near Yellow-Green Group 146A. Under surface color: commonly near Yellow-Green Group 146C more or less suffused with near Greyed-Orange Group 176A.

*Adult foliage*.—Upper surface color: commonly near Yellow-Green Group 147A. Under surface color: commonly near Yellow-Green Group 147B.

Leaflets:

*Shape*.—Tip: cuneiform. Base: rounded.

*Texture*.—Leathery.

*General appearance*.—Oval.

*Edge*.—Slightly denticulate.

*Serration*.—Small and single.

*Petiole rachis*.—Length: commonly near 2 to 5 cm on average. Diameter: commonly near 0.1 cm on average. Texture: little bit glandulous with few small thorns. Color of upper surface: commonly near Yellow-Green Group 146B. Color of under surface: commonly near Yellow-Green Group 146B.

*Petioles*.—Diameter: approximately 0.1 to 0.2 cm on average. Upper surface: no glandular. Under surface: few prickles. Color of upper surface: commonly near Yellow-Green Group 146B. Color of under surface: commonly near Yellow-Green Group 147B. Petiole length of terminal leaflet: commonly near 2.0 to 3.5 cm on average.

*Stipules*.—General appearance: adnate, pectinate and narrow. Length: approximately 1.5 to 2.0 cm on average. Width: approximately 0.2 cm on average. Color of upper surface: commonly near Green Group 137B. Color of under surface: commonly near Green Group 137D.

Inflorescence:

*Number of flowers per stem*.—Generally between 1 and 3 flowers per stem.

*Bud*.—Shape: conical. Length: approximately 2.5 cm on average. Width: approximately 2.0 cm on average. Color as calyx breaks: Upper surface: commonly near Red Group 53A. Under surface: commonly near Red Group 53B.

*Sepals*.—Length: approximately between 2.5 to 3.0 cm on average. Width: approximately 1.1 cm on average. Shape: some narrow and obovate and denticulate extensions, at the top: longish and narrow, at the base: upright. Upper surface: Texture: tomentous. Color: commonly near Green Group 143C. Under surface: Texture: glandular. Color: commonly near Green Group 143C.

*Receptacle*.—Color: commonly near Green Group 143C. Length: approximately 0.4 cm on average. Width: approximately 1.0 to 1.2 cm on average. Surface: smooth. Shape: funnel shaped.

*Peduncle*.—Length: approximately 4.5 to 6.0 cm on average. Width: approximately 0.4 cm on average. Surface: glandular. Color: commonly near Green Group 143C.

*Flower*.—Height: approximately near 3 to 5 cm on average. Average diameter when fully open: approximately near 10 to 12 cm on average. Shape: cup shaped. Number of petals under normal conditions: approximately 30 to 40 petals on average. Shape of the petal: base: obtuse. top: rounded. Texture of the petal: leathery. Petal length: approximately 3 to 4 cm on average. Petal width: approximately 3 to 4 cm on average. Petal shape: rounded. Petal margin: medium reflexing with undulation. Petal arrangement: imbricated with some petaloids. Petal drop: petals drop off cleanly before drying. Petaloids: number is commonly 5 to 8 on average; length is approximately 1 to 3 cm on average; width is approximately 0.2 to 2.5 cm on average; shape is commonly 1 to 2 are rounded, 1 to 2 are cordate, 2 to 3 are half-cordate; apex and margin are medium to strong undulation of margin (not reflexing); color is commonly near Red Group 53A on the upper surface and commonly between Red Group 53D and Red Purple Group 59D on the under surface. Fragrance: strong, fruity fragrance. Color when opening: Upper surface: commonly near Red-Purple Group 66A to Red-Purple Group 74A; spot at the base is commonly between Yellow Group 13B and Yellow Group 13C. Under surface: commonly near Red-Purple Group 67A; spot at the base is commonly near Yellow Group 12C. Color of the open flower: Upper surface: commonly near Red-Purple Group 66A; spot at the base is commonly between Yellow Group 13B and Yellow Group 13C. Under surface: commonly near Red-Purple Group 67B; spot at the base is near Yellow Group 12C. Anthers: number is approximately 192 on average, length is approximately 0.2 cm on average, coloration is commonly near Yellow-Orange Group 17A, and arrangement is regular around styles. Filaments: length is approximately 0.4 to 0.8 cm on average and coloration is commonly near Yellow-Orange Group 16D. Styles: length is approximately 0.4 cm on average, the coloration is commonly near Red Group 52A, and the number is approximately 163 on average. Stigmas: size is approximately 0.3 cm on average and the coloration is commonly near Yellow-Orange Group 17C. Pollen: coloration is commonly near Greyed-Yellow Group 160A. Hips: not available at this stage.

Development:

*Vegetation*.—Strong.

*Blooming*.—Early in the season, very abundant and nearly continuous.

*Tolerance to disease*.—Good, and particularly against Oidium and mildew.

The new 'MEIZOLNIL' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Hybrid Tea rose plant characterized by the following combination of characteristics:

(a) very abundantly and nearly continuously forms attractive, cup-shaped, dark pink blossoms which emit a very pleasant strong fragrance, (b) forms attractive, rather dense, glossy foliage, (c) exhibits good tolerance to diseases, particularly against Oidium and mildew, and (d) is well suited for providing attractive ornamentation; substantially as herein shown and described.

* * * * *

MEIZOLNIL